(12) United States Patent
Abu Bakar et al.

(10) Patent No.: US 8,551,309 B2
(45) Date of Patent: Oct. 8, 2013

(54) AMPEROMETRIC BIOSENSOR FOR HISTAMINE DETERMINATION

(75) Inventors: Fatimah Abu Bakar, Selangor (MY); Abu Bakar Salleh, Selangor (MY); Rahman Wagiran, Selangor (MY); Mai Keow Ching, Selangor (MY); Yook Heng Lee, Selangor (MY); Anuar Ahmad, Selangor (MY); Rosnin Mustaffa, Selangor (MY)

(73) Assignee: Universiti Putra Malaysia, Selangor Darul Ehsan (MY)

( * ) Notice: Subject to any disclaimer, the term of this patent is extended or adjusted under 35 U.S.C. 154(b) by 662 days.

(21) Appl. No.: 12/531,550

(22) PCT Filed: Mar. 19, 2008

(86) PCT No.: PCT/MY2008/000019
§ 371 (c)(1),
(2), (4) Date: Sep. 16, 2009

(87) PCT Pub. No.: WO2008/115044
PCT Pub. Date: Sep. 25, 2008

(65) Prior Publication Data
US 2010/0096277 A1    Apr. 22, 2010

(30) Foreign Application Priority Data

Mar. 21, 2007  (MY) ................................ PI20070441

(51) Int. Cl.
*G01N 27/327*    (2006.01)
(52) U.S. Cl.
USPC ................ 204/403.14; 205/777.5; 435/25
(58) Field of Classification Search
USPC .................. 205/777.5, 778, 780.5, 787, 792; 204/403.01, 403.14, 412; 435/25
See application file for complete search history.

(56) References Cited

U.S. PATENT DOCUMENTS

| 5,565,329 A | 10/1996 | Ohashi et al. |
| 5,571,395 A * | 11/1996 | Park et al. ................. 204/403.1 |
| 2003/0217928 A1 * | 11/2003 | Lin et al. ....................... 205/109 |

FOREIGN PATENT DOCUMENTS

| JP | 2000-266717 | 9/2000 |
| JP | 2001-061497 | 3/2001 |
| JP | 2001-099803 | 4/2001 |
| JP | 2002-000264 | 1/2002 |
| WO | WO 01/02827 | 1/2001 |

OTHER PUBLICATIONS

Keow, C. M., et al., "An amperometric biosensor for the rapid assessment of histamine level in tiger prawn (*Penaeu monodon*) spoilage" Food Chemistry, vol. 105, No. 4, 2007, p. 1636-1641.*
P. Bouvrette, et al., "Amperometric biosensor for diamine using diamine oxidase purified from porcine kidney", Enzyme and Microbial Technology vol. 20, 1997, p. 32-38.*
K. B. Male, et al., "Amperometric Biosensor for Total Histamine, Putrescine and Cadaverine using Diamine Oxidase", Journal of Food Science, vol. 61, No. 5, 1996, p. 1012-1016.*
L. Sim Beam, et al., "Photocurable ferrocene-containing poly(2-hydroxyl ethyl methacrylate) films for mediated amperometric glucose biosensor", Thin Solid Films, vol. 477, 2005, p. 104-110.*
Lange et al., "Enzyme sensor array for the determination of biogenic amines in food samples," Analytical and Bioanalytical Chemistry, Jan. 2002, vol. 372, No. 2, pp. 276-283.
Hart et al., "Some Recent Designs and Developments of Screen-Printed Carbon Electrochemical Sensors/Biosensors for Biomedical, Environmental, and Industrial Analysis," Analytical Letters, vol. 37(5), pp. 789-830.

* cited by examiner

*Primary Examiner* — J. Christopher Ball
(74) *Attorney, Agent, or Firm* — Preti Flaherty Beliveau & Pachios LLP

(57) ABSTRACT

There is provided by this invention a simple and rapid amperometric biosensor for determining the level of histamine in seafood or fish. The biosensor combines the technology of screen-printing with immobilized diamine oxidase as the bioreceptor. IQ one embodiment of the present invention, the biosensor incorporates potassium hexacyanoferrate (III) as a mediator.

31 Claims, 6 Drawing Sheets

AMPEROMETRIC BIOSENSOR FOR HISTAMINE DETERMINATION

1. TECHNICAL FIELD OF THE INVENTION

The present invention relates to an amperometric biosensor for the determination of histamine, particularly in seafood and fish tissues.

2. BACKGROUND OF THE INVENTION

Seafood and fish products are important for their nutritional value and also as item of international trade and foreign exchange earnings for a number of countries in the world. Unlike other animal products, the quality of seafood and fish products are more difficult to control due to their variations in species, sex, age, habitats and the action of their autolytic enzymes (Venugopal, 2002). The levels of histamine have been suggested as rapid seafood and fish products spoilage indicators (Male et al., 1996; Tombelli and Mascini, 1998; Patange et al., 2005). Histamine was observed to accumulate in seafood and fish tissues when bacteria spoilage commenced during storage of the products (Male et al., 1996) without altering the seafood and fish normal appearance and odor (Lehane and Olley, 2000). Therefore, simple and rapid techniques for determining the levels of histamine in seafood and fish products are in great demand by the food industry in order to estimate the products freshness.

Histamine exerts its effects by binding to receptors on cellular membranes in the respiratory, cardiovascular, gastrointestinal and haematological immunological system and the skin in the course of allergic and causes reactions such as hypotension, flushing, diarrhea, vomiting and headache (Lehane and Olley, 2000). The symptoms may vary between individuals exposed to the same dose of histamine in contaminated seafood and fish products (Bremer et al., 2003). The US FDA international food safety regulation has quoted 500 ppm as the hazardous level of histamine (FDA, 2001). However, histamine is generally not uniformly distributed in a decomposed fish (Lehane and Olley, 2000; FDA, 2001). Therefore, guidance level of 50 ppm has been set as the chemical index for seafood and fish spoilage. If 50 ppm of histamine is found in one section of the seafood or fish tissues, there is the possibility that other sections may exceed 500 ppm (Lehane and Olley, 2000; FDA, 2001). The seafood and fish products with histamine above that level are prohibited from being sold for human consumption (Gigirey et al., 1998).

Several methods have been proposed for histamine detection such as the routine chromatography analysis, which includes gas chromatography, thin layer liquid chromatography, reversed phase liquid chromatography, liquid chromatography with pre-column, post-column or on-column derivatisation technique and high pressure liquid chromatography (Chemnitius and Bilitewski, 1996; Male et al., 1996; Scott, 1998; Tombelli and Mascini, 1998). However, these methods require complicated and expensive instruments, toxic reagents, time consuming and are not practical for in situ analysis due to the complex sample treatment and requires a trained personnel to carry out such tests.

An amperometric system based on screen-printed electrodes would allow the production of simple, inexpensive and portable devices for rapid seafood and fish product freshness and spoilage determination. Amperometric biosensors measure the electron flow of the oxidation or reduction of an electro-active species. The steady state current is proportional to the concentration of the electro-active species. In the field of enzyme electrodes, the most widely use enzymes are oxidases that produce electro-active hydrogen peroxide, which can be measured by a current signal (Willner et al., 2000) or direct electrochemical communication of a substrate with the enzyme. Amperometric biosensors have been found to overcome most of the other types of biosensor disadvantages. The amperometric biosensors can be operated in turbid media, have comparable instrument sensitivity and are more amenable to miniaturization (Chaubey and Malhotra, 2002).

3. SUMMARY OF THE INVENTION

It is a primary object of the present invention to provide a simple and rapid amperometric biosensor, which is capable of determining the freshness and spoilage of seafood and fish products by determining the levels of histamine in seafood and fish tissues.

It is also an object of the present invention to provide a miniaturized and sensitive amperometric biosensor, which is capable of determining the levels of histamine in seafood and fish tissues under a low operation voltage.

Another object of the present invention is to provide a convenient and safe method for determining the levels of histamine in seafood and fish tissues that can be performed in non-laboratory settings.

These and other objects of the present invention are achieved by,

An amperometric biosensor for histamine determination comprising a working electrode, a counter electrode and a reference electrode, wherein the working electrode is a screen-printed electrode, characterized in that diamine oxidase is immobilized on the surface of the screen-printed working electrode.

An amperometric biosensor for histamine determination comprising a working electrode, a counter electrode and a reference electrode, wherein all of the electrodes are screen-printed onto a substrate, characterized in that diamine oxidase and potassium hexacyanoferrate (III) are immobilized and electro deposited on the surface of the screen-printed working electrode.

A method for histamine determination, comprising the steps of applying a sample suspected to contain histamine to any one of the biosensors described above and measuring the current to provide an output signal indicative of the presence of histamine.

4. BRIEF DESCRIPTION OF THE ACCOMPANYING DRAWINGS

Other aspects of the present invention and their advantages will be discerned after studying the detailed description in conjunction with the accompanying drawings in which.

5. DETAILED DESCRIPTION OF THE INVENTION

Figure 6:
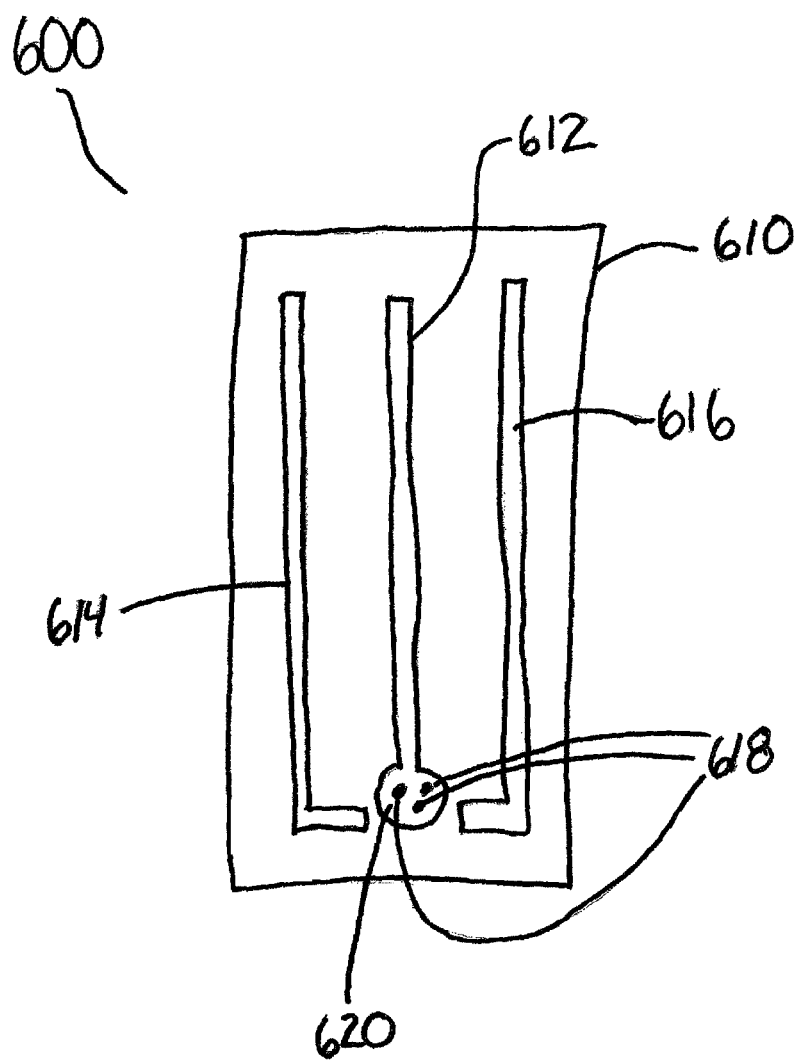
FIG. 6 is a block diagram of an amperometric biosensor in accordance with an embodiment of the present invention.

The present invention provides an amperometric biosensor for determining the level of histamine in a sample wherein immobilized diamine oxidase is used as the bioreceptor. In the first embodiment of the present invention, referring now to FIG. 6, a biosensor 600 comprises a substrate 610 with a screen-printed working electrode 612, a counter electrode 614 and a reference electrode 616 disposed thereon. Preferably, the biosensor 600 comprises a carbon paste based screen-printed working electrode 612, a platinum rod counter electrode 614 and a silver/silver chloride (Ag/AgCl) reference electrode 616.

Diamine oxidase 618 is immobilized on the surface of the screen-printed working electrode 612 by poly (2-hydroxyethyl methacrylate) (photoHEMA) 620. Before immobilization, the enzyme is dissolved in 0.1M phosphate buffer in a range of pHs from 6.4 to 8.4, with the optimum pH of 7.4. PhotoHEMA is prepared as reported by Low and coworkers (2005). 2-hydroxyethyl methacrylate (HEMA) is mixed with photoinitiator 2' dimethoxyphenylacetophenone (DMPP). This mixture is shaken until all the DMPP dissolves. The homogenized photosensitive mixture is covered with aluminum foil and stored at 4° C. until use to avoid degradation by UV light. For bio-receptor preparation, an appropriate volume of photoHEMA is mixed with diamine oxidase solution. According to the present invention, diamine oxidase solution is mixed with photoHEMA according to the ratio of one part of diamine oxidase to four parts of photoHEMA (1:4). Less photoHEMA concentrated mixture with ratios of diamine oxidase solution to photoHEMA of 1:1, 1:2 and 1:3 showed inconsistent current changes while insufficient enzyme (ratio of 1:5) decreased the current changes. The homogenized mixture is then drop-coated onto the surface of the working electrode 612 and the working electrode 612 is photo-cured in an UV-exposure unit under nitrogen gas flow for approximately 300 seconds. If the working electrode 612 is cured less than 300 seconds, it will dry incompletely and may cause the enzyme to leach. Exposing the working electrode 612 under UV for more than 300 seconds may decrease the enzyme activity.

The present biosensor detects histamine in a sample by the oxidation deamination process of the histamine, forming imidazole acetaldehydes and subsequently imidazole acetic acid as shown below:—

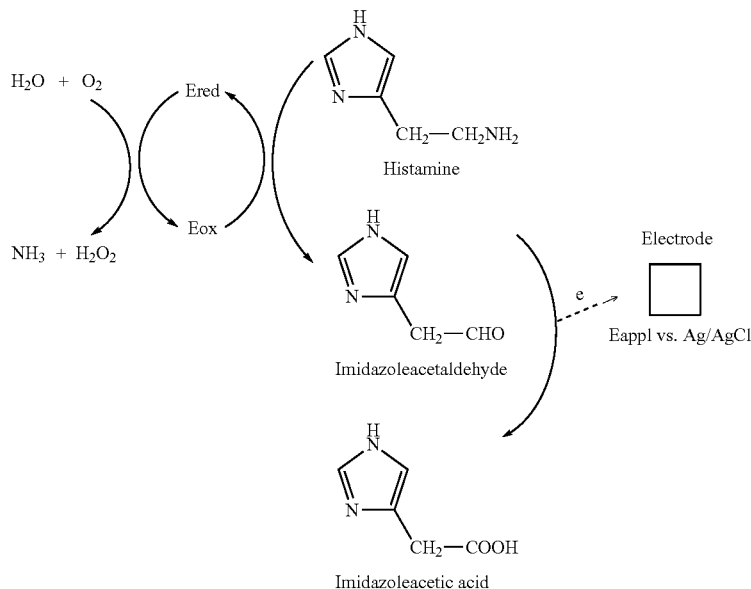

The activity between diamine oxidase and histamine in the above reaction causes a direct electrochemical communication between the substrate and the enzyme. The electron transfer mechanism occurs via the electro-oxidation of the formed product; imidazole acetaldehyde, which is highly unstable and oxidized to imidazole acetic acid.

Figure 1:
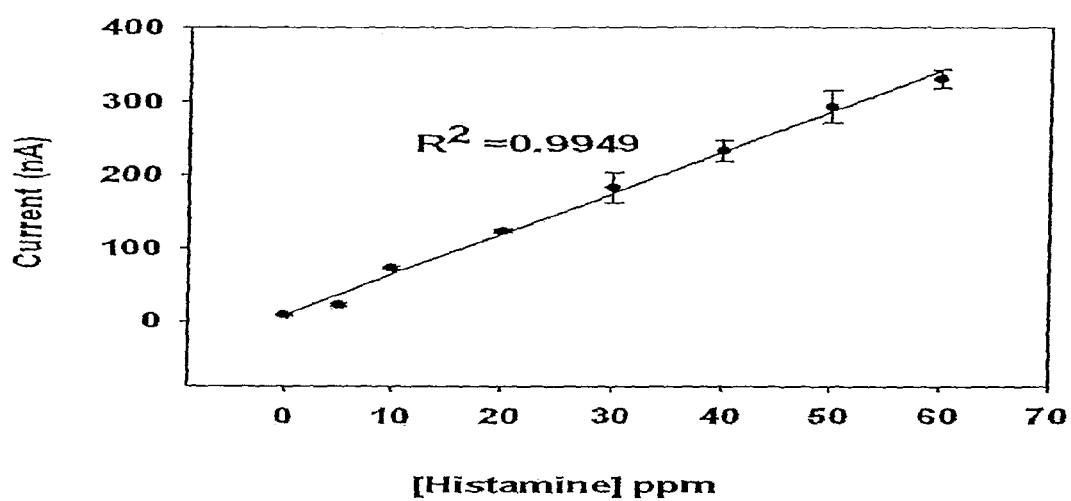
FIG. 1 is a graph showing the linear response range of the amperometric biosensor of one embodiment of the present invention.
Figure 2:
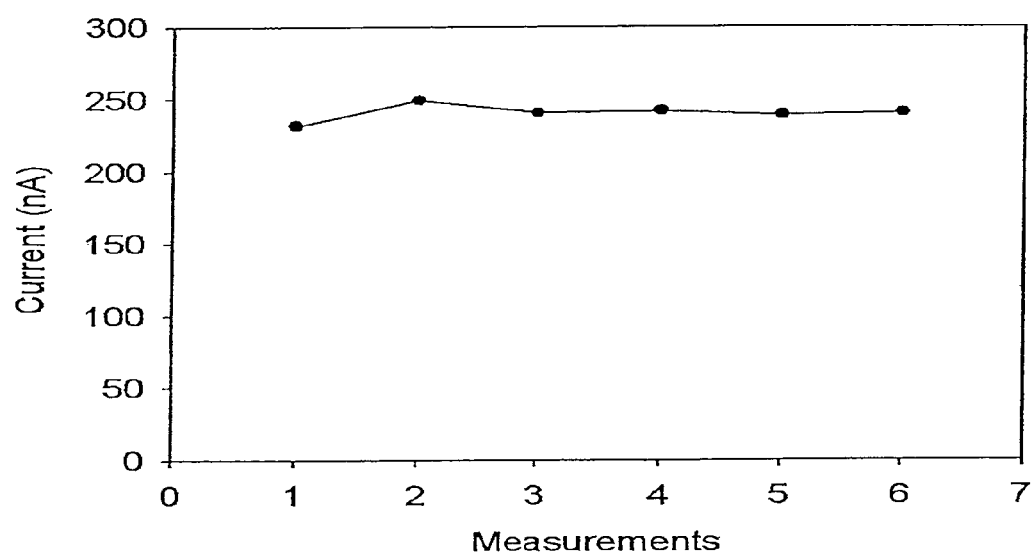
FIG. 2 is a graph showing the current readings obtained after consecutive measurements were performed with the same biosensor.

The biosensor has a response range of up to 300 ppm of histamine. The linear response range as shown in FIG. 1 shows that the analytical range of the biosensor is up to 60 ppm of histamine. This covers the seafood and fish products spoilage indication level of 50 ppm of histamine as quoted by the FDA, US. The linear response range of the biosensor is broader compared to reports by Takagi and Shikata (2004); Frebort et al. (2000); Carsol and Mascini (1999); Draisi et al. (1998) and Chemnitius and Bilitewski (1996) using flow injection method or Clark oxygen electrode. The sensitivity of the biosensor is 5.56 nA ppm$^{-1}$ with a limit of detection as low as 0.65 ppm of histamine, calculated as three times of the standard deviation at the zero analyte response. The stability of the biosensor also proved to be optimal since several analyses can be performed with the same electrodes without significant decrease in the current readings as shown in FIG. 2.

Figure 3:
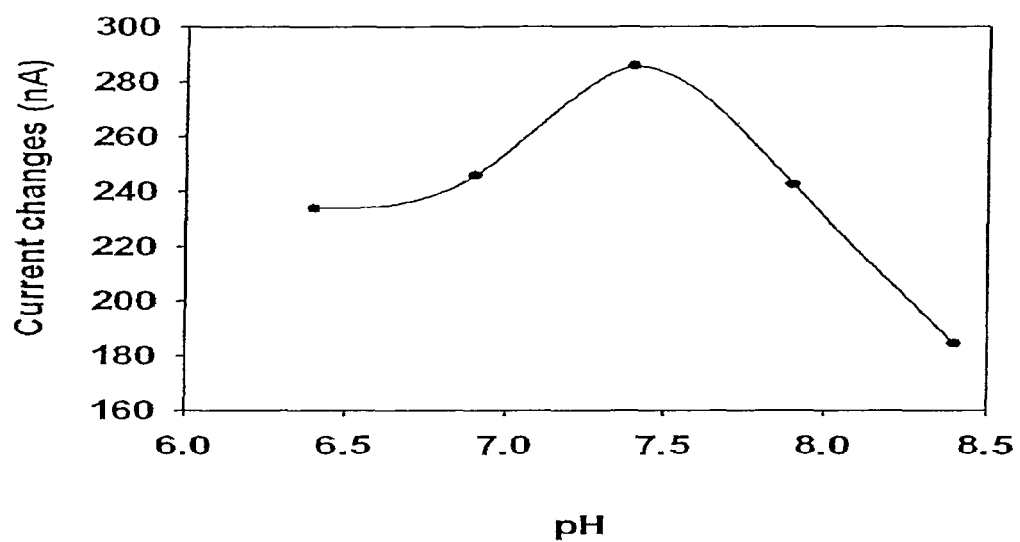
FIG. 3 is a graph showing the effect of pH on the response of the developed biosensor.
Figure 4:
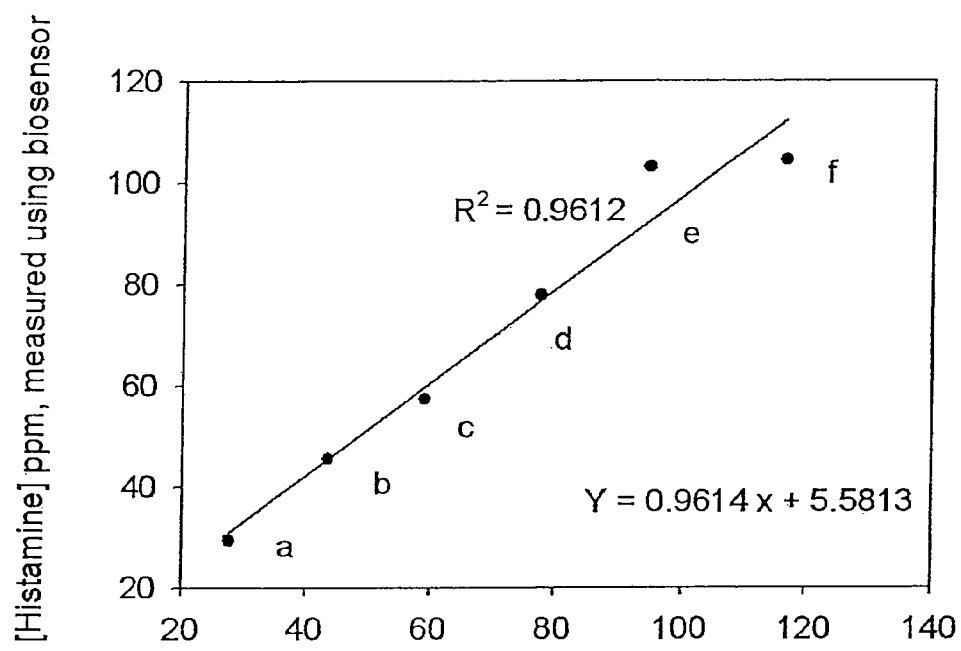
FIG. 4 is a graph showing the correlation of histamine levels determined by the biosensor embodying the invention and high performance liquid chromatography (HPLC).

The level of histamine in a sample is determined by applying the sample to the biosensor and measuring the current output signal. Histamine determination is carried out at a potential range from 0.30 volt to 0.50 volt. The optimum potential for histamine determination using immobilized enzyme is 0.35 volt. The electron transfer mechanism at 0.35 volt occurs via the electro-oxidation of the formed product, imidazole acetaldehyde and as proposed by Kapeller-Adler and Fletcher (1959), imidazole acetaldehyde is highly unstable and unlikely to exist; therefore, it is able to be oxidized by diamine oxidase as well (Lehane and Olley, 2000). The current output of the developed biosensor is pH dependent and can be detected at a pH range of 6.4 to 8.4. However, optimum activity is observed at pH 7.4 as shown in FIG. 3. The current output also increase following the reaction time, starting from 20 seconds and 50 seconds is the optimum reaction time for histamine determination. The accuracy of histamine determination using the present biosensor is compared to the conventional high performance liquid chromatography (HPLC) method with 95% confidence level. The correlation of histamine levels determined by the biosensor and established HPLC method is shown in FIG. 4.

In the second embodiment of the present invention, the three-electrode system of the biosensor is miniaturized by screen-printing technology. Miniaturized biosensor offers several advantages, such as only small amount of enzyme is required for the fabrication of the biosensor, mass production of such miniaturized biosensor is possible and consequently disposable-type of biosensor may be realized. The present miniaturized biosensor comprises a working electrode, a counter electrode and a reference electrode wherein all of the electrodes are screen-printed onto a substrate. Preferably, the biosensor comprises carbon paste based screen-printed working and counter electrodes and a silver chloride (AgCl) paste based screen-printed reference electrode. All three electrodes are screen-printed onto a polyester substrate.

Diamine oxidase is immobilized on the surface of the screen-printed working electrode by poly (2-hydroxyethyl methacrylate) (photoHEMA) as described in the previous embodiment. The present biosensor is modified from the previously described biosensor by the use of potassium hexacyanoferrate (III) as a mediator to increase the sensitivity of the biosensor. Potassium hexacyanoferrate (III) is electrodeposited on the surface of the screen-printed working electrode by cyclic voltammetry method. The electrode is cycled at least fifteen times in a solution of 0.1 M potassium hexacyanoferrate (III) dissolved in deionized water at 0.2 vs$^{-1}$ with stirring. The modified electrodes are then washed and rinsed with a large volume of deionized water and stored dry at room temperature until use.

The present biosensor detects histamine in a sample by the electron flow of the mediator as shown below:—

Potassium hexacyanoferrate (III) is employed as a mediator for the biosensor due to its excellent bioelectrochemical properties. $[Fe(CN)_6]^{3-}$ is easily reduced to $[Fe(CN)_6]^{4-}$. This property allows the deposition of both oxidized $[Fe(CN)_6]^{3-}$ and reduced $[Fe(CN)_6]^{4-}$ on the surface of the screen-printed working electrode. Hydrogen peroxide is produced on the surface of the electrode when immobilized diamine oxidase reacts with histamine as shown on equation 1 below:—

$$Histamine + O_2 + H_2O \xrightarrow{DAO} Imidazoleacetaldehyde + NH_3 + H_2O_2 \quad (1)$$

$$H_2O_2 + 2 Fe(CN)_6^{4-} + 2 H^+ \longrightarrow 2 H_2O + 2 Fe(CN)_6^{3-} \quad (2)$$

$$2 Fe(CN)_6^{3-} + e \longrightarrow Fe(CN)_6^{4-} \quad (3)$$

The following process (equation 2) occurs due to the capability of mediators such as electron acceptors to catalyze the reduction of oxygen to hydrogen peroxide. The $[Fe(CN)_6]^{3-}$ is then reduced to $[Fe(CN)_6]^{4-}$ as shown in equation 3 for reuse.

Figure 5:
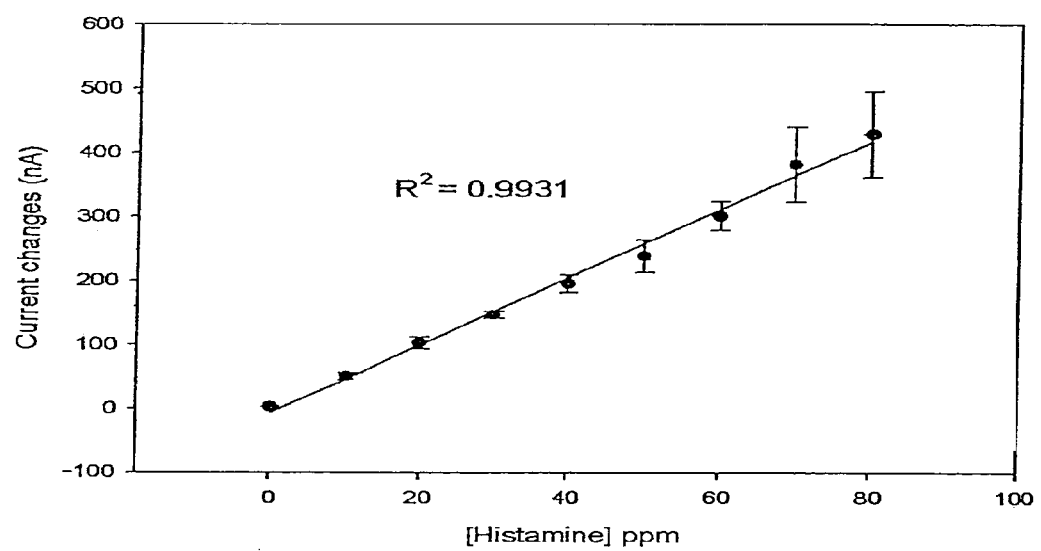
FIG. 5 is a graph showing the linear response range of the amperometric biosensor of another embodiment of the present invention.

The present biosensor has a response range of up to 200 ppm of histamine. The linear response range as shown in FIG. 5 shows that the biosensor detects a broader range of histamine of up to 80 ppm compared to the previous embodiment. The sensitivity of the biosensor is 5.31 nA ppm$^{-1}$. The operation condition of the biosensor is as described in the previous embodiment where the potential range is from 0.30 volt to 0.50 volt, preferably at 0.35 volt; the pH range is from 6.4 to 8.4, preferably pH 7.4; and the reaction time starts from 20 seconds with 50 seconds as the optimum reaction time for histamine determination.

The following examples are intended only to further illustrate the invention and are not intended to limit the scope of the invention, which is defined by the claims.

Real Samples Analysis

Tiger prawns (*Penaeus monodon*) were exposed at 30° C.±2° C. from 0 to 5 hours and samples were collected every hour. The prawn's shell, head and tail were removed and approximately 10 g of the prawn's body region was blended with 100 ml of phosphate buffer, 0.1 M, pH 7.4. The samples were then analyzed using the developed biosensors without any pretreatment or extraction step. Measurements were performed using an Autolab PGSTAT 12 Potentiostat/Galvanostat with GPES software operated at 0.35 volt. The samples were tested in a beaker containing phosphate buffer 0.1 M, pH 7.4.

Meanwhile, high performance liquid chromatography (HPLC) method required histamine to be extracted from the

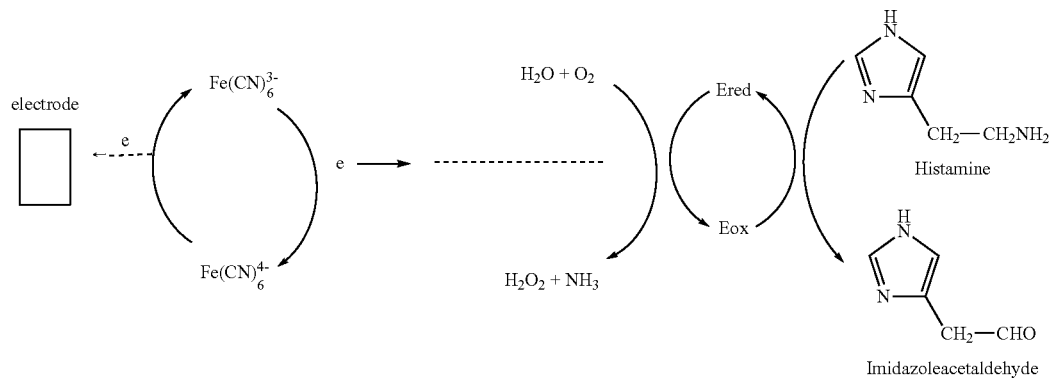

samples as described by Mopper and Sciacchitano (1994). The samples were blended with methanol and diluted according to a ratio of one extract to ten deionized water (1:10). The purification of histamine was then carried out as reported by Vale and Gloria (1997). Finally, the extracted samples were derivatized to increase the detection of benzoylated ring at 254 nm (Hauschild, 1993). Separation of benzoylated histamine was carried out by isocratic reversed-phase HPLC using a Waters 1500 Series HPLC Pump and a 4.6 mm×250 mm I.D. $C_{18}$ column, particle size 5 μm, at which histamine was detected spectrophotometrically at 254 nm with a Water Model 2487 Dual λ Absorbance Detector.

Fabrication of Miniaturized Biosensor

Thick film technology was applied in the construction of the miniaturized biosensor because it permits construction of solid-state, mechanically robust and planar sensors. This is achieved through the sequential deposition of thick films on a substrate by screen printing process. The configuration of the biosensor comprises layers of paste deposited sequentially onto an insulating support or substrate. The present miniaturized biosensor was manufactured by a multi-stage screen-printing process using a semi-automated DEK-J202RS thick film printer. High modulus mesh of monofilament polyester (SEFAR® PET 1000) stencil (specification of 90-48 W) was designed as a straight, short and wide conductor parallel with square pads confirmed to the screen mesh. This provides better conductivity compared to designs with curved and narrow conductor with circular pads. The stainless steel screen mesh (78 μm fabric thickness) was mounted at 45° to the print stroke with an emulsion thickness of 12 μm±2 μm for the printed pastes. The three electrodes were screen-printed onto the polyester substrate (50×60 mm). Prior to the printing process, the polyester sheets were baked in the oven at 130° C. for 5 hours to avoid shrinking of the foil during subsequent heating steps. Each printing cycle produced three miniaturized screen-printed electrodes with carbon paste (Screen Technology, BBI 440) working and counter electrodes and silver chloride (AgCl) paste (Dupont, B166) reference electrode on a single piece of polyester substrate. A silver layer (Dupont, B111) was printed as a basal track layer to increase the conductivity and adhesion of the pastes on the substrate. The pastes were dried in the oven at 110° C. for 10 minutes after each layer was printed to drive-off the solvents.

While particular embodiments of the subject invention have been described, it will be obvious to those skilled in the art that various changes and modifications to the subject invention can be made without departing from the scope of the invention. It is intended to cover, in the appended claims, all such modifications that are within the scope of this invention.

What is claimed is:

1. An amperometric biosensor for histamine determination comprising:
    a substrate;
    a screen-printed working electrode screen-printed onto a surface of the substrate,
    a counter electrode disposed on the surface of the substrate;
    a reference electrode disposed on the surface of the substrate; and
    a coating of diamine oxidase immobilized with poly (2-hydroxyethyl methacrylate) (photoHEMA) disposed on a surface of the screen-printed working electrode,
    wherein the coating of immobilized diamine oxidase comprises a ratio of diamine oxidase to photoHEMA of 1:4.

2. The biosensor of claim 1, wherein the screen-printed working electrode is carbon paste based.

3. The biosensor of claim 1, wherein the counter electrode is a platinum rod.

4. The biosensor of claim 1, wherein the reference electrode is a silver/silver chloride (Ag/AgCl) electrode.

5. A method of immobilizing diamine oxidase on a surface of a screen-printed working electrode, the method comprising:
    a) mixing a diamine oxidase solution with poly (2-hydroxyethyl methacrylate) (photoHEMA) with a ratio of diamine oxidase to photoHEMA of 1:4;
    b) drop-coating the mixture onto a surface of the screen-printed working electrode; and
    c) photo-curing the screen-printed working electrode.

6. The method of claim 5, further comprising dissolving diamine oxidase in phosphate buffer before mixing with poly (2-hydroxyethyl methacrylate) (photoHEMA).

7. The method of claim 5, wherein photo-curing the screen-printed working electrode comprises photo-curing in a UV-exposure unit under nitrogen gas flow for 300 seconds.

8. A method of histamine determination, comprising the steps of:
    a) applying a sample suspected to contain histamine to the biosensor of claim 1; and
    b) measuring a current to provide an output signal indicative of the presence of histamine.

9. The method of claim 8, wherein a voltage for histamine determination is in a range from 0.30 volt to 0.50 volt.

10. The method of claim 9, wherein the voltage for histamine determination is approximately 0.35 volt.

11. The method of claim 8, wherein a pH for histamine determination is in a range from 6.4 to 8.4.

12. The method of claim 11, wherein the pH for histamine determination is approximately 7.4.

13. The method of claim 8, wherein a reaction time for histamine determination is at least 20 seconds.

14. The method of claim 13, wherein the reaction time for histamine determination is approximately 50 seconds.

15. An amperometric biosensor for histamine determination comprising:
    a substrate;
    a working electrode screen-printed onto a surface of the substrate;
    a counter electrode screen-printed onto the surface of the substrate;
    a reference electrode screen-printed onto the surface of the substrate;
    a coating of diamine oxidase immobilized with poly (2-hydroxyethyl methacrylate) (photoHEMA) on a surface of the screen-printed working electrode; and
    potassium hexacyanoferrate (III) electrodeposited on the surface of the screen-printed working electrode,
    wherein the coating of immobilized diamine oxidase comprises a ratio of diamine oxidase to photoHEMA of 1:4.

16. The biosensor of claim 15, wherein the screen-printed working and counter electrodes are carbon paste based.

17. The biosensor of claim 15, wherein the screen-printed reference electrode is silver chloride (AgCl) paste based.

18. The biosensor of claim 15, wherein the substrate comprises a polyester substrate.

19. The biosensor of claim 15, further comprising a silver layer printed as a basal track layer on the surface of the substrate.

20. The biosensor of claim 15, wherein diamine oxidase is immobilized via drop-coating with poly (2-hydroxyethyl methacrylate) (photoHEMA) according to the following steps:
- a) mixing diamine oxidase solution with poly (2-hydroxyethyl methacrylate) (photoHEMA);
- b) drop-coating the mixture onto the surface of the screen-printed working electrode; and
- c) photo-curing the screen-printed working electrode.

21. The biosensor of claim 20, wherein diamine oxidase is dissolved in phosphate buffer before mixing with poly (2-hydroxyethyl methacrylate) (photoHEMA).

22. The biosensor of claim 20, wherein the working electrode is photo-cured in a UV exposure unit under nitrogen gas flow for 300 seconds.

23. The biosensor of claim 15, wherein potassium hexacyanoferrate (III) is electrodeposited by cyclic voltammetry method, comprising the step of cycling the screen-printed working electrode in a solution of potassium hexacyanoferrate (III) with stirring.

24. The biosensor of claim 23, wherein the working electrode is cycled at least fifteen times in a solution of 0.1 M potassium hexacyanoferrate (III) dissolved in deionized water at 0.2 $vs^{-1}$ with stirring.

25. A method of histamine determination, comprising the steps of:
- a) applying a sample suspected to contain histamine to the biosensor of claim 15; and
- b) measuring a current to provide an output signal indicative of the presence of histamine.

26. The method of claim 25, wherein a voltage for histamine determination is in a range from 0.30 volt to 0.50 volt.

27. The method of claim 26, wherein the voltage for histamine determination is approximately 0.35 volt.

28. The method of claim 25, wherein a pH for histamine determination is in a range from 6.4 to 8.4.

29. The method of claim 28, wherein the pH for histamine determination is approximately 7.4.

30. The method of claim 25, wherein a reaction time for histamine determination is at least 20 seconds.

31. The method of claim 30, wherein the reaction time for histamine determination is approximately 50 seconds.

* * * * *